(12) United States Patent
Lister et al.

(10) Patent No.: US 7,737,328 B2
(45) Date of Patent: *Jun. 15, 2010

(54) **TRANSFORMATION AND REGENERATION OF *ALLIUM* PLANTS**

(75) Inventors: Carolyn Elizabeth Lister, Christchurch (NZ); Colin Charles Eady, Christchurch (NZ)

(73) Assignee: New Zealand Institute for Crop & Food Research Limited, Christchurch (NZ)

( * ) Notice: Subject to any disclaimer, the term of this patent is extended or adjusted under 35 U.S.C. 154(b) by 606 days.

This patent is subject to a terminal disclaimer.

(21) Appl. No.: 11/494,734

(22) Filed: Jul. 28, 2006

(65) Prior Publication Data

US 2007/0192894 A1 Aug. 16, 2007

Related U.S. Application Data

(63) Continuation of application No. 09/890,064, filed as application No. PCT/NZ99/00214 on Dec. 10, 1999, now Pat. No. 7,112,720.

(30) Foreign Application Priority Data

Jan. 29, 1999 (NZ) .................................. 333992

(51) Int. Cl.
*C12N 15/84* (2006.01)
*C12N 15/82* (2006.01)
*C12N 15/31* (2006.01)
*A01H 4/00* (2006.01)

(52) U.S. Cl. .................. 800/294; 800/282; 800/288; 800/300; 435/430.1; 435/469

(58) Field of Classification Search ................ None
See application file for complete search history.

(56) References Cited

FOREIGN PATENT DOCUMENTS

| JP | 92-060496/08 | 1/1992 |
| WO | WO 92/06205 | 4/1992 |
| WO | WO 97/42333 | 11/1997 |
| WO | WO 98/44136 | 10/1998 |
| WO | WO 99/10512 | 3/1999 |

OTHER PUBLICATIONS

Hansen et al. Trends in Plant Science 4(6): 226-231 (Jun. 1999).*
Potrykus, I. Bio/Technology 8(6): 535-542 (Jun. 1990).*
Narasimhulu et al. The Plant Cell 8: 873-886 (May 1996).*
Eady, C. New Zealand Journal of Crop and Horticultural Science 23(3): 239-250 (1995).*
Eady, C. pp. 53-67 In: Molecular Methods of Plant Analysis, vol. 20 (Genetic Transformation of Plants), Jackson et al, eds., Springler-Verlag: Berlin (2003).*
Eady et al. Plant Cell Reports 24(4): 209-215 (2005).*
Hong et al. Plant Cell, Tissue and Organ Culture 43(1): 21-28 (1995).*
Nagasawa et al. Plant Cell, Tissue and Organ Culture 15(2): 183-187 (1988).*
Dunstan et al. Scientia Horticulturae 11(1): 37-43 (1979).*
Nagakubo et al. Plant Cell, Tissue and Organ Culture 32(2): 175-183 (1993).*
Fujieda et al. Journal of the Faculty of Agriculture of Kyushu University 22(1-2): 89-98 (1977).*
Dong et al. *Allium* Improvement Newsletter 7: 12-14 (1997).*
Kim et al. Plant Science 114(2): 215-220 (1996).*
Eady et al. Transformation of Onion (*Allium cepa* L.) Proceedings of the 1998 National Onion (and other *Allium*) Research Conference, Ronald E. Voss, ed., University of California, p. 91-94.
Eady et al.; *Agrobacterium tumefaciens*-mediated transformation of leek (*Allium porrum*) and garlic (*Allium sativum*), Plant Cell Reports, DOI 10.1007; Jan. 12, 2005.
Eady, et al., Transient expression of uidA constructs in in vitro onion (*Allium cepa* L.) cultures following particle bombardment and *Agrobacterium*-mediated DNA delivery, Plant Cell Reports, vol. 15, No. 12, 1996, pp. 958-962.

* cited by examiner

*Primary Examiner*—David T Fox
(74) *Attorney, Agent, or Firm*—Finnegan, Henderson, Farabow, Garrett & Dunner, L.L.P.

(57) ABSTRACT

The invention relates to a novel transformation method for plants of the genus *Allium*. Plants transformed by the method are also provided. The method preferably involves an *Agrobacterium tumefaciens*-mediated transformation, involving the transformation of immature embryos as the explant source and wherein the method is carried out without passage through the callus phase.

10 Claims, 6 Drawing Sheets

TRANSFORMATION AND REGENERATION OF *ALLIUM* PLANTS

The is a continuation application of U.S. patent application Ser. No. 09/890,064, filed Oct. 31, 2001, now U.S. Pat. No. 7,112,720, which is a national stage application of International Application PCT/NZ99/00214, filed Dec. 10, 1999, which claims priority to New Zealand Application Serial. No. 333992, filed Jan. 29, 1999.

FIELD OF INVENTION

The invention relates to a method of transforming plants of the Allium family and more particularly to the transformation of onion plants. The invention also relates to the transformed plants.

BACKGROUND OF THE INVENTION

There are no published protocols for the transformation and regeneration of *Allium* species. The *Allium* crop species are probably the most economically important vegetable species for which transformation technology is unavailable. For other major vegetable crops, confirmed transformation systems have been produced.

Initially, many monocotyledons were thought to be unsusceptible to *Agrobacterium*-mediated transformation. The development of direct gene transfer techniques soon led to bombardment being the favoured method of monocotyledon transformation. However, direct gene transfer is not without its problems. Often, low transformation frequencies and a high frequency of unusual integration patterns has been observed in transgenic plants. Recently, *Agrobacterium*-mediated transformation of monocotyledons has gained favour and many monocotyledonous species (including rice; wheat, barley, maize and sugarcane) have now been transformed using this method. A key component in the success of these systems has been the transfer of DNA to callus cell types (usually derived from the pre culture of embryo tissue) followed by regeneration from these callus cells using precise post transformation selection protocols. Transformation of *Allium* callus is not useful as regeneration from callus is extremely difficult.

Recently, Haseloff (1997) has modified the gfp gene to enhance its use as a transgenic marker gene in viable plant systems. Green fluorescent protein (GFP) enables researchers to follow precisely the fate of any cells expressing this gene and so optimise post transformation cell survival. Such a system has been useful in the development of the onion transformation protocol reported here.

As monocotyledons, the *Allium* species were predisposed to be recalcitrant to transformation. Onions (*Allium cepa* L) are a crop with diverse environmental requirements. It has, therefore, been relatively understudied with respect to the application of biotechnology. There are only a few reports of DNA delivery to *Alliums* (Klein 1987; Dommisse et al. 1990; Eady et al. 1996; Barandiaran et al. 1998). Three workers used direct gene transfer whilst Dommisse et al. (1990) demonstrated that *Agrobacterium*-mediated transformation may be possible. Recently some reports of regeneration protocols for *Alliums* that are appropriate for transformation study have become available (Hong and Deberg 1995; Xue et al. 1997; Eady et al. 1998; Saker 1998). Only one report exists on the development of potential selective agents for use in *Allium* transformation (Eady and Lister 1998a).

OBJECT OF THE INVENTION

It is therefore an object of the invention to provide a method for producing transgenic *Allium* plants or to at least provide the public with a useful choice.

In this specification we report the first repeatable protocol for the production of transgenic *Allium* plants.

SUMMARY OF THE INVENTION

The invention provides a method of transforming *Allium* plants.

Preferably, the invention provides an *Agrobacterium tumefaciens*-mediated transformation method for *Allium* plants.

In particular, the invention provides a method of transforming plants of the *Allium* genus comprising inoculating an embryo culture of an *Allium* species with an *Agrobacterium tumefaciens* strain containing a suitable vector or plasmid.

In particular, the invention provides a method of transforming plants of the *Allium* genus comprising the following steps:
 (a) delivering previously manipulated DNA into embryo, or embryo derived culture cell types of the *Allium* genus via vector or direct gene transfer;
 (b) selecting transformed plant material;
 (c) culturing and regenerating the transformed plants;

wherein the transformation is carried out without passage through a callus phase.

Preferably embryos are inoculated immediately following their isolation.

Preferably the transformed plants are onions (*Allium cepa* L).

Preferably immature embryos are used as the explant source.

Preferably the embryos are transformed using a binary vector and more preferably a binary vector carrying a selectable gene.

The embryos may preferably be transformed with a herbicide selective gene. Examples include the bar gene or ppt gene encoding resistance to phosphinothricin or genes encoding resistance to glyphosate. However other genes may be used.

The embryos could alternatively be transformed with an antibiotic selective gene. An example is the kanamycin or geneticin resistance gene, nptll.

In particular, the invention provides a method of transforming *Allium* using immature embryos as an explant source, including:
 a) isolating immature embryos of the *Allium* plant to be transformed;
 b) inoculating the immature embryos with an *Agrobacterium tumefaciens* strain containing a binary vector;
 c) wounding embryos and infiltrating embryos with *Agrobacteria*;
 d) transferring embryos to a selective medium;
 e) culturing embryo pieces;
 f) selecting putative transgenic cultures; and
 g) regenerating phenotypically normal plants.

The invention also provides transformed *Allium* plants. Preferably the *Allium* plants are transformed using protocols in line with the method of the invention. Callus: uniform Undifferentiated mass of dividing plant cells (Walden, R. (1988). In: Genetic transformation in plants. Oxford University Press, ISBN 0-335-15822-6) or a tissue arising from disorganized proliferation of cells either in culture or in nature. As opposed to a culture which consists of growing cells, tissues, plant organs, or whole plants in nutrient medium under aseptic conditions e.g. embryo culture (Plant tissue culture: theory and practice. Ed Bhojwani, S. S and Razdan, M. K. 1983, Elsevier) i.e. population of differentiated proliferating cells.

BRIEF DESCRIPTION OF THE DRAWINGS

Embodiments of the invention are now described, by way of example only, with reference to the drawings in which:

FIG. 5 probed with gfp probe. FIG. 6 probed with bar gene probe. Lane 1 and 2, 1 and 5 copy number controls of plasmid pBINmgfpER respectively (containing gfp gene), Lane 3 non-transgenic onion DNA. Lane 4-6 clones of a transformant selected from experiment 994, Lane 7-9 clones of a transformant from experiment 9911. Lane 10-12 control transgenic plants containing the gfp gene and not the bar gene. Lane 13-14, 5 and 10 copy controls of plasmid containing the bar gene (lane 11-14 over washed the gfp probed blot).

DETAILED DESCRIPTION OF THE INVENTION

Materials and Methods

Figure 1:
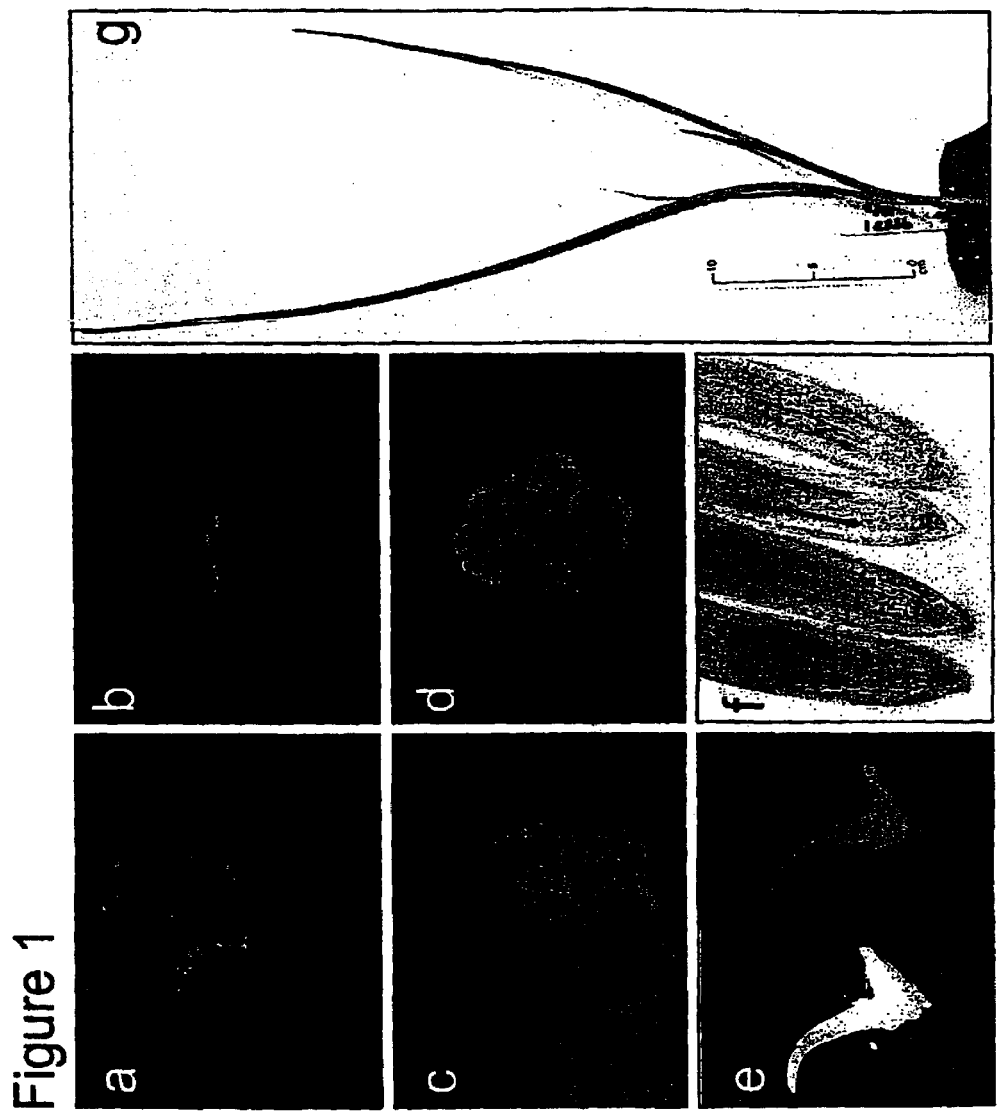
FIGS. 1a-1g show a) GFP expression in embryo tissue after 5 days of cocultivation (×50). b) GFP expression after 2 weeks (×50). c) GFP sector after 6 weeks culture (×25). d) Independent GFP positive tissue (×5). e) GFP positive onion shoot culture (×5). f) Two GFP negative (left) and two GFP positive (right) roots from independent plants (×10). g) Transgenic onion plant (×0.2).

Plant material: Field grown, open-pollinated umbels of *Allium cepa* L. were used as a source of immature embryos. Immature embryos were isolated as described by Eady et al. (1998).

Bacterial strain: *Agrobacterium tumefaciens* strain LBA4404 containing the binary vector pBIN m-gfp-ER (Haseloff 1997) or binary vectors derived from p Cambia series were used. Cultures were grown to log phase in LB media containing an appropriate antibiotic and then stored at −80° C. in 1 ml aliquots containing 15% glycerol. Aliquots were used to innoculate 50 ml overnight cultures. The following morning cultures were replenished with an equal volume of LB containing antibiotic and 100 µM acetosyringone and grown for a further 4 hours. *Agrobacteria* were isolated by 10 minute centrifugation at 4500 rpm and resuspended in an equal volume of P5 (Eady and Lister 1998a) containing 200 µM acetosyringone.

Transformation procedure: Isolated immature embryos were isolated in groups of 20-40, cut into approximately 1 mm sections and then transferred into 0.8 ml of *Agrobacteria* and vortexed for 30 seconds. Following this treatment, embryos were placed under vacuum (~20 in. Hg) for 30 minutes before blotting dry on sterile Whatman #1 filter paper and then transfer to solid P5 medium (Eady and Lister 1998) (~40 embryos per plate). After 6 days cocultivation, embryo pieces were transferred to P5 plus 10 mg/l geneticin and 200 mg/l timentin or 5 mg/l of Basta (active ingredient phosphothricin) and 200 mg/l of timentin depending on which binary vector was used. These embryo pieces were cultured in the dark under the same conditions as described for the production of secondary embryos (Eady et al. 1998). Cultures were transferred to fresh medium every 2 weeks. After 3-4 transfers, growing material was transferred to P5 plus 25 mg/l geneticin or 5 mg/l Basta depending on the binary vector used and grown for a further 8 weeks. During this time pieces of putative transgenic tissue that were obviously actively growing were transferred to regeneration medium (Eady et al. 1998). Shoot cultures were maintained for 12 weeks and developing shoots were transferred to ½MS media (Murashige and Skoog 1962) plus 20 mg/l geneticin or 5 mg/l of Basta as appropriate to induce rooting. Rooted plants were either transferred to ½MS plus 120 g/l sucrose to induce bulbing or transferred to soil in the glasshouse (12 h 12-23° C. day, 12 h 4-16° C. night).

Analyses for transformation: For GFP expression, tissue was examined by observation under a fluorescence microscope (excitation 475 nm, emission 510 nm Haseloff et al. 1997). Larger tissues with high levels of expression were observed using hand held "shirt pocket" fluorescent lanterns (Zelco industries inc., 630 So. Columbus Ave, Mt Vernon N.Y. 10551-4445). Nptll expression was determined by the ability of regenerating plantlets to form roots on ½MS containing geneticin, bar expression was determined by the ability of regenerating plantlets to form roots on ½ MS containing Basta.

DNA isolation was performed using a nucleon phytopure plant DNA extraction kit (Amersham Lifescience; Buckinghamshire, England). Southern analysis followed the method of Timmerman et al. (1993) and used PCR-amplified probes to confirm the presence of the gfp, nptll and bar genes.

Genomic DNA from the onions was digested with HindIII, which cuts once in the middle of the T-DNA.

Cytology: Chromosome counts were made from the root tips of 2 primary transformants and followed the procedure of Grant et al. (1984).

EXAMPLE 1

Transformation and Characterisation of Primary Transgenic Tissue

After three days of cocultivation, single cells expressing GFP could be observed in tissue transformed with T-DNA containing the mgfpER gene. Attempts to count cells expressing GFP after 5 days were abandoned as the variation within treatments and between embryo pieces was huge, with many embryo pieces showing no fluorescence and some exhibiting hundreds of fluorescing cells (FIG. 1a). In the latter case, distinguishing between multicellular 'stable' transformation events and multiple adjacent single-celled 'transient' events was not possible. Thus, large biases in any measurement of initial transfer could have occurred. As an alternative, treatments were given an initial transfer rating: * being excellent initial transfer (⁻20-30% of tissue pieces with >20 GFP positive cells per plate),  represented average initial transfer (5-20% of tissue pieces with some GFP positive cells per plate, and * being poor initial transfer (<5% of tissue pieces with GFP positive cells per plate) (Table 1). Contamination was a problem in many experiments. Often whole experiments (data not shown) had to be abandoned due to contamination, much of which probably arose from infected embryos.

sible and ranged from * in contaminated samples to *** in non-contaminated samples. Indeed, lack of good initial transfer was often an early indication of contamination. Eady et al. (1998) and Eady and Lister (1998ab) demonstrated that genotype, condition of the embryo, size of the embryo, cocultivation conditions and selection pressure all affect embryo survival. The combined effects of these parameters and their interaction with the transformation process will, until they can be controlled, continue to make the success of onion transformation susceptible to large variation.

EXAMPLE 2

Regeneration

After 6 weeks of culture, tissue was transferred to a selective medium without timentin. No growth of *Agrobacterium* was observed in any of the cultures grown on this medium. Fluorescing sectors continued to grow on this media and after 2 transfers it was possible to isolate the first sectors free from non-fluorescing cells (FIG. 1c). As sectors became independent (FIG. 1d) they were transferred to regeneration medium. A few sectors still attached to non-fluorescing tissue were also transferred. On regeneration medium transgenic cultures responded in the same way as non-transgenic, embryo-derived cultures (Eady et al. 1998). Multiple shoots formed on many of the independent transgenic cultures. However, some, particularly the slower growing or more friable dedifferentiated cultures, either failed to regenerate or produced highly hyperhydric shoots that could not be transferred to the glasshouse. Up to 29% of stable sectors produced shoot cultures

TABLE 1

Summary of 5 transformation experiments.

| Expt | N°. of embryos | % of embryos contaminated | Initial transfer | N°. of multicellular GFP tissue pieces 4 wk | 8 wk | Independent plants | Positive Southern# |
|---|---|---|---|---|---|---|---|
| 1 | ~400 | 100 | * | — | — | — | — |
| 2 | ~360 | 40 | *** | 52 (16)a | 15 (4.6) | 2 (0.6) | 1 of 1 tested |
| 3 | ~440 | 0 | *** | 72 (16) | 44 (10) | 12 (2.7) | 8 of 8 tested |
| 4 | ~520 | 60 | ** | a | 11 (2.4) | 3 (0.7) | 2 of 2 tested |
| 5 | ~200 | 100 | * | — | — | — | — |

* - poor,
** - average,
*** - excellent initial transfer, see text for details. Numbers in brackets represent the percentage of transformants from uncontaminated embryos (a - represents the stage and treatments which were transferred to the wrong selective media for 4 days).

After 2 weeks on selection medium, embryo pieces-transformed with pBINmgfpER construct were screened for GFP expression and only pieces containing fluorescing cells were maintained (FIG. 1b). The vast majority of fluorescing cells died over the following four weeks. Some fluorescing cells divided into multicellular clusters of up to ⁻50 before their ability to fluoresce gradually faded. One interpretation of this was that the transformed cells were still reliant on surrounding non-transgenic cells, which died due to selection pressure and could no longer support the transgenic cells. The number of stable transgenic sectors arising from different plates within experiments varied from 0 to 21 and reflected the numerous parameters that affect the onion transformation process. Comparison between experiments was initially posfrom which plants could be obtained (Table 1). These responses to regeneration are typical of those seen in non-transformed embryogenic cultures (Eady et al. 1998). Actively growing shoots were transferred to rooting medium containing an appropriate selective agent. In the instances where non-fluorescing cells were also transferred to shoot media some shoots were produced that failed to root on geneticin. These did not fluoresce. All plants that formed actively growing roots on geneticin also fluoresced (FIG. 1f), indicating that in all instances the complete T-DNA was transferred. Fluorescence in the differentiated structures varied, with most fluorescence being seen in root tips. In shoots, strong fluorescence was limited to young shoots (FIG. 1e). However, GFP fluorescence in shoots was usually masked by red autofluorescence from the chlorophyll. The presence of GFP fluorescence in older leaves could sometimes be observed in the stomatal guard cells.

The multiple shoot cultures enabled clonal plants from independent transgenic events to be grown. This was particularly important as earlier attempts to exflask putative transgenic plants had failed (Eady and Lister 1998b). In the first successful transformation experiment described here only 4 from 48 transgenic plants transferred to the soil have died. A total of 14 independent transformants have been transferred to the containment glasshouse.

EXAMPLE 3

Analyses of Transformants from Plants Transformed with pBINmgfpER

Figure 2:
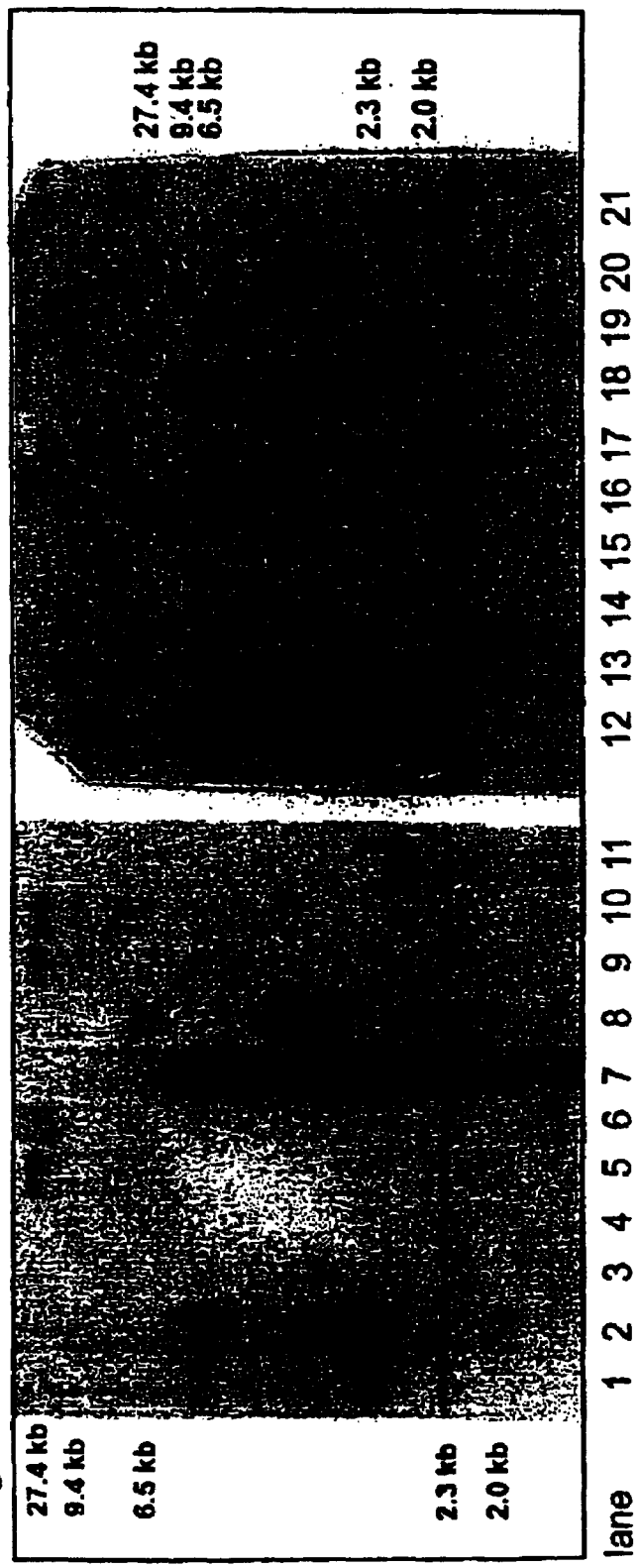
FIG. 2 shows Southern analysis of the gfp gene of primary transformants: Bluescript plasmid containing the gfp gene (uncut), 1 copy number control (lane 1), 10 copy number control. (lane 2), blank (lane 3), non transgenic onion (lane 4), 7 transgenic onion plants (lanes 5-11), bluescript plasmid containing the gfp gene (uncut), 1 copy number control (lane 12), 10 copy number control (lane 13), blank (lane 14), non transgenic onion (lane 15), 6 transgenic onion plants (lanes 16-21).

Apart from fluorescence and growth on geneticin, transformation of onion plants was confirmed by Southern analysis, probing with the gfp gene (FIG. 2). As HindIII cuts the T-DNA only once it was possible to show copy number from the Southern analysis. Ten of the 13 transformants shown have single copies. The other 3 have 2 (lane 8), 3 (lane 18) and multiple copies (lane 7). Lanes 19 and 21 are from clonal shoots and, as expected, they show the same pattern. EcoR1 digest and subsequent Southern analysis liberated an expected internal T-DNA fragment of ~900 bp.

Chromosome counts in the 2 primary transformants tested showed a diploid (2n=16) chromosome complement.

EXAMPLE 4

Evidence that the Transgenic Onion Plants Transformed with the pBINmgfpERantiroot Contain the Antisense Root Alliinase Gene Construct.

Onion immature embryos were transformed according to the protocol of Eady et al (1999) with the pBINmgfpER plasmid (Haseloff 1997) modified to contain the antisense root alliinase gene construct. The BamH1 to Kpn1 fragment of the root alliinase gene was cloned into the BamH1-Kpn1 sites in the cloning vector pART7. This gave a antisense version of the root alliinase sequence under control of the CaMV35s regulatory element and ocs termination sequence in pART7. The not1 fragment of this modified pART7 (containing the above CaMV35s promoter-antisense root alliinase-ocs termination) was then cloned into the Hind111 site of pBINmgfpER. Digestion of this plasmid (pBINmgfpERantiroot) with BamH1 to liberate a 1.6 Kb fragment was used to determine presence and orientation of the insert. PBINmgfpERantiroot was electroporated into *Agrobacterium tumefaciens* strain LBA4404 and grown on kanamycin to select for transformants. Presence of the binary vector was confirmed by plasmid isolation and PCR for the gfp gene. LBA4404 (pBINmgfpERantiroot) was used in transformation experiments.

Six putative transformants that fluoresced (to indicate the presence of the gfp gene) and grew on media containing geneticin (to indicate presence of the nptll gene) were obtained from three experiments. Three of these transformants or clones thereof were analysed by Southern Blot analysis for the successful transfer of the T-DNA insert from the binary vector by probing with both gfp and nptll gene probes. Roots from these plants were also analysed biochemically for root alliinase enzyme activity following the protocol of Clark et al (1998) (Table 2). Western Blots of the desalted protein (0.5 µg/lane) extracts were probed with an anti-alliinase antibody and visualised colourmetrically using a goat-antirabbit-alkaline phosphatase system to determine the relative levels of alliinase enzyme in the transgenic plants.

TABLE 2

| Plant | Alliinase activity (U/mg protein) |
|---|---|
| Non transgenic CLK control (9910) | 14.0 |
| transformant 992.11F1 | 3.4 |
| transformant 994.7G1 | 11.9 |
| transformant 992.11F2 | 9.6 |
| transformant 992.9A1 | 6.3 |

Results

1. Southern Analysis

Figure 3:
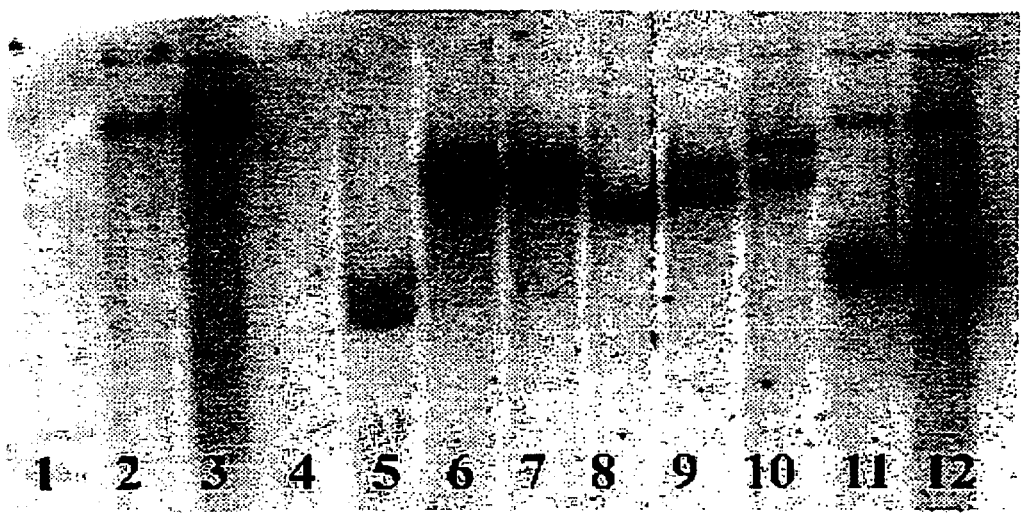
FIG. 3 shows a Southern blot transgenic antisense root alliinase plants probed with the gfp gene fragment to indicate the presence of the pBINmgfpERantiroot T-DNA sequence. Lane 1 lambda hindlll marker; lane 2 one copy equivalent control pBINmgfpERantiroot, lane 3 five copy control pBINmgfpERantiroot; lane 4 non transformed onion, lane 5 positive control onion transformed with pBINmgfpER; lane 6-10 transgenic plants transformed with pBINmgfpERantiroot (6&7 and 9&10 are separate clones); lane 11 one copy equivalent control pBINmgfpERantiroot, lane 12 five copy control pBINmgfpERantiroot.

All three plants analysed contained at least one copy of the T-DNA sequence containing the antisense root alliinase DNA sequence (FIG. 3) indicating that integration of modified alliinase sequences into *Allium* species had been achieved. Both nptll and gfp sequences which flanked the antisense alliinase gene on the T-DNA could be deleted indicating successful transfer of the complete T-DNA in all cases.

Figure 4:
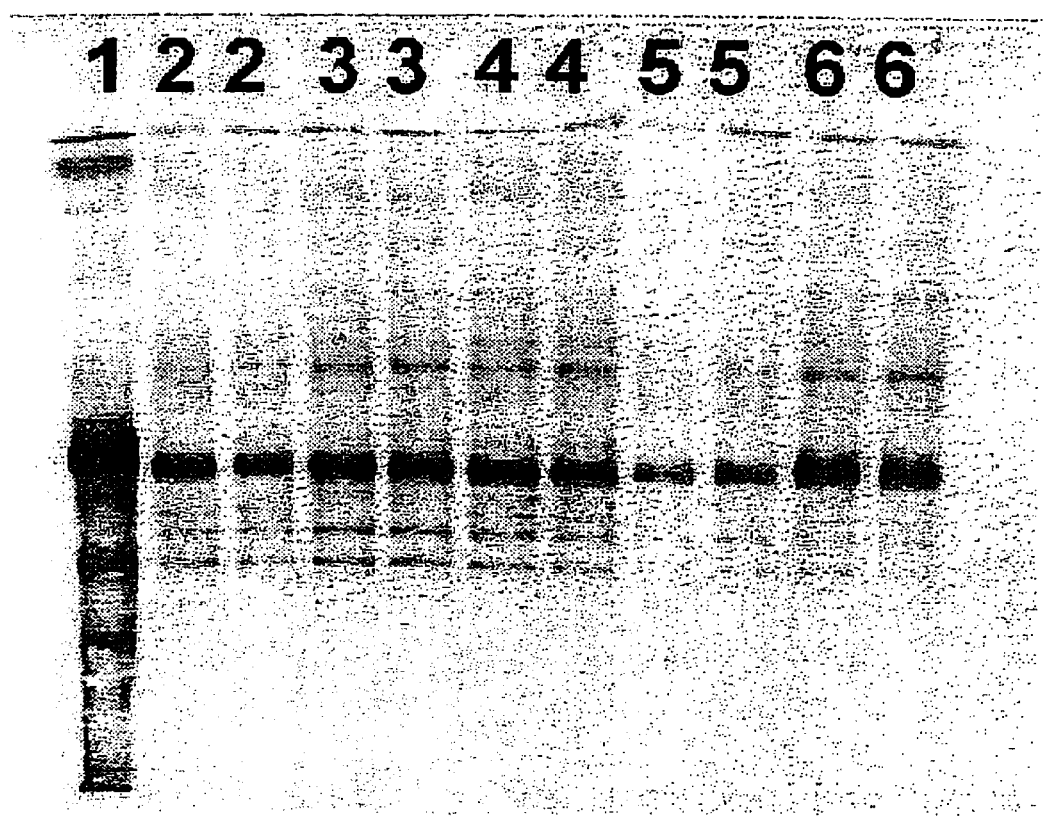
FIG. 4 shows a Western blot analysis of alliinase levels in the roots of transgenic and non transgenic onion roots. Lane 1 purified root alliinase control; Lane 2-5 alliinase levels from the roots of four transgenic plants transformed with the pBINmgfpERantiroot DNA; Lane 6 alliinase levels from the roots of a typical non transgenic control plant.

The Western blot of FIG. 4 shows the relative amounts of the root alliinase in protein extracts taken from the transgenic and control roots. These extracts were run on a 10% SDS page gel to separate the proteins and then transferred to nitrocellulose paper using standard techniques. This was then incubated with rabbit polyclonal antibodies raised against the purified alliinase (Clark S. A. 1993. Molecular cloning and cDNA encoding alliinase from onion (*Allium cepa* L.), Ph D. thesis, University of Canterbury, Christchurch, New Zealand). These antibodies have been shown to bind specifically to the alliinase protein. Goat anti-rabbit alkaline phosphatase was added to specifically bind this antibody and after washing, the membrane was immersed in NBT (4 nitrotetrazolium chloride) and BCIP (5 bromo 4 chloro 3 indolyl phosphate) for 30 minutes in the dark. Colour develops at the site of the phosphatase in proportion to the amount alliinase present. The Western blot therefore shows the relative amounts of alliinase protein present in the roots of the transgenic and control onion plants. The control onion plant has the greatest colour development and has the most alliinase per unit of root protein. The intensity relates to the activity of the enzyme shown in the table and indicates that the activity is related to the amount of alliinase protein and not changes in enzyme activity. This is what is expected when using antisense technology to reduce enzyme activity.

EXAMPLE 5

Transformation of Onions to Confer Herbicide Resistance.

Onion immature embryos were transformed according to the protocol with the plasmid pCambia3301 modified, using standard cloning techniques, to contain the mgfpER reporter gene construct instead of the gus reporter gene. This construct, contained within its T-DNA region the bar gene encoding resistance to the herbicide phosphinothricin and the visual reporter gene mgfpER both under regulatory control of the CaMV35s promoter. In two separate experiments, 994 and 9911 onion immature embryos from cultivar Cron 19 and CLK respectively were transformed with the above construct. In experiment 994 transformants were selected using the visual marker (GFP expression) and growth on herbicide, whilst on P5 media only. In experiment 9911 only selection on herbicide was used to select for transformation. Selection conditions in both experiments consisted of growth on P5 media containing 5 mg/l of the herbicide Basta (containing phosphinothricin) and 200 mg/l of timentin for 4-6 weeks with fortnightly subculture. Following this, cultures were transferred to P5 media plus 5 mg/l Basta for a further 4 weeks of culture. Cultures were then transferred to SM4 media for 6 weeks. In experiment 9911 the SM4 media included 5 mg/l Basta. Shoots from 9911 were rooted on ½ MS30 plus 5 mg/l Basta. Shoots from experiment 994 were just rooted in ½ MS30. Once vigorous root growth was established plants were transferred to the glasshouse.

Results

Further to examples 1-5, additional transgenic plants containing variations of the antisense alliinase construct (outlined in example 4) have been produced in additional cultivars CRON 12, CRON19 and CRON2. The nature of these plants has been confirmed by GFP expression where appropriate and regeneration on media containing geneticin. A summary of the plants produced in all the examples outlined above is given in table 3 to demonstrate the plasticity of the transformation system. In experiments that were not contaminated transgenic plants have been obtained from all cultivars so far tested.

TABLE 3

Illustrating the different binary vectors, T-DNA, cultivars and selective agents used in the *Allium* transformation protocol outined and the measures taken thus far to determine the nature of the transformants.

| Experiment number | Binary vector used for transformation (T-DNA in brackets) | Cultivar used | Number of independent transformed lines produced | Number of plants produced | GFP +ve | Growth on selective agent (geneticin or Basta) | Southern Analysis and probe used |
|---|---|---|---|---|---|---|---|
| 98/7, 8, 9 | pBIN(mgfpER) | CLK | >10 | >100 | yes | yes (geneticin) | 12/12 tested (gfp) |
| 99/2 | pBIN(antiroot-mgfpER) | CRON12 | 3 | >40 | yes | yes (geneticin) | 5/5 tested (gfp & nptII) |
| 99/3 | pBIN(35santibulb-mgfpER) | CRON19 | 1 | 12 | yes | yes (geneticin) | yet to be tested |
| 99/3 | pBIN(35santibulb-mgfpER) | CRON2 | 3 | 7 | yes | yes (geneticin) | yet to be tested |
| 99/4 | pBIN(antiroot-mgfpER) | CRON19 | 1 | 3 | yes | yes (geneticin) | yet to be tested |
| 99/4 | pCambia3301 (modified) | CRON19 | 1 | 10 | yes | ? (phosphinothricin) | 3/3 (gfp) tested 0/3(bar) tested |
| 99/6 | pCambia3301 (modified) | CRON12 | 1 | 2 | yes | ? (phosphinothricin) | Yet to be tested |
| 99/6 | pBIN(antiroot-mgfpER) | CRON12 | 1 | 1 | yes | yes (geneticin) | yet to be tested |
| 99/7 | pBIN(mgfpER) | CRON19 | 1 | >12 | yes | yes (geneticin) | yet to be tested |
| 99/11 | pCambia3301 (modified) | CLK | 3 | >10 | ? | Yes (phosphinothricin) | 3/3 (gfp & bar) tested |
| 99/12 | pBIN(bulbpromoterantibulb-mgfpER) | CLK | 1 | 1 | yes | yes | yet to be tested |

(Basta = phosphinothricin)

Figure 5:
FIGS. 5 and 6 show a Southern blot analysis of HindIII digested DNA from Onion plants transformed with the modified pCambia 3301 T-DNA.
Figure 6:
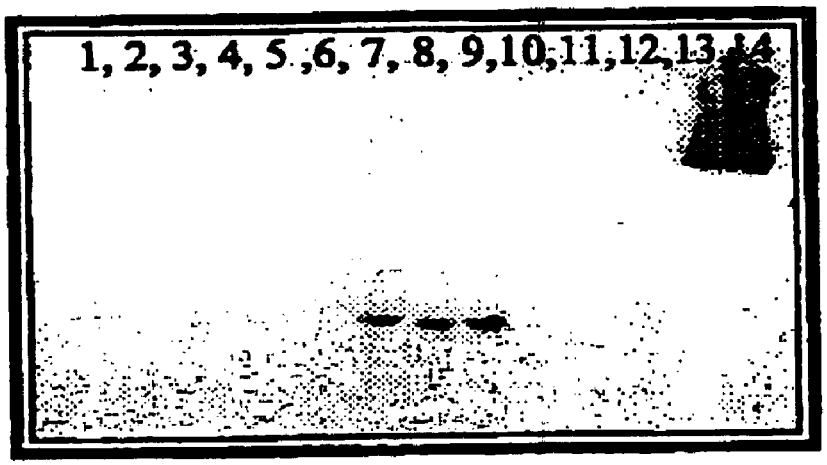
Figure 7:
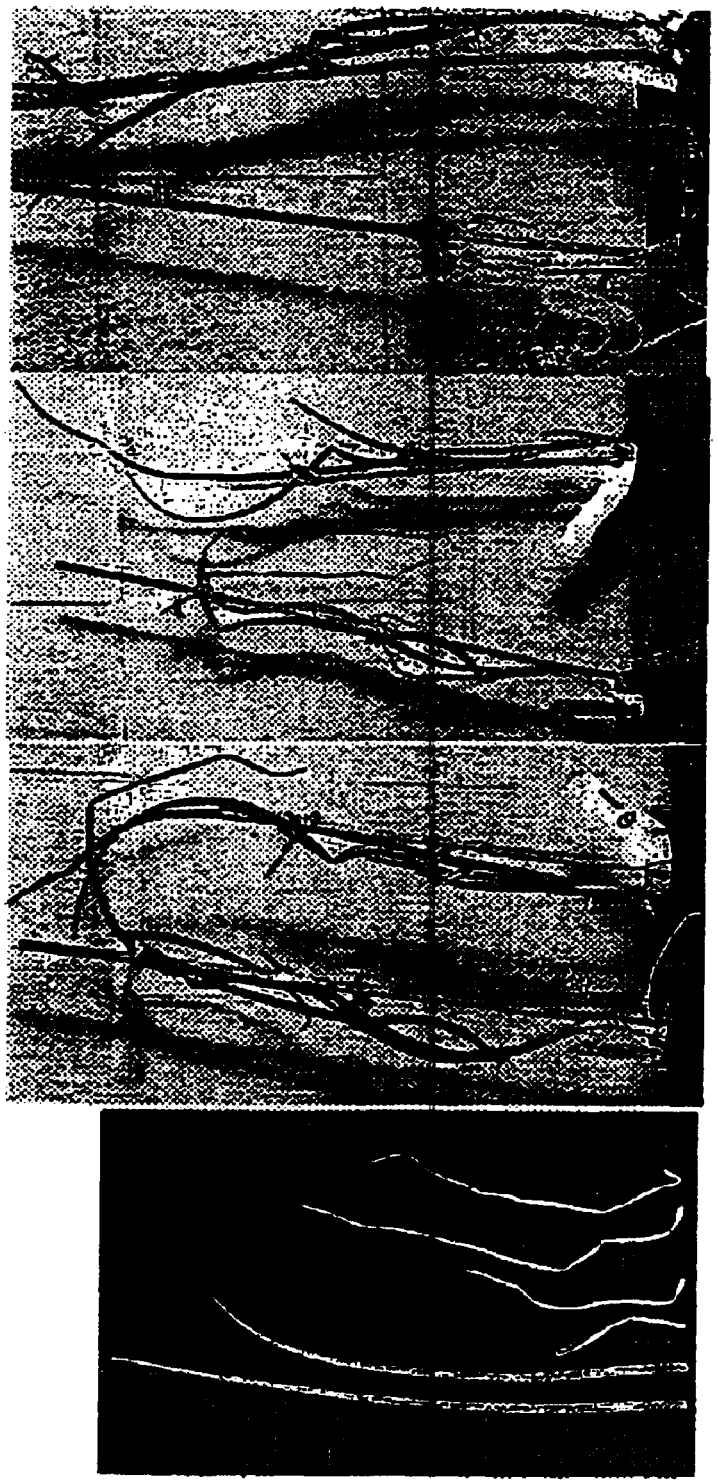
FIGS. 7A-7D show a comparison between A, an onion leaf containing the bar gene (two on left) and onion leaves without the bar gene (four on right) 10 days after painting with 0.5% v/v solution of the herbicide Buster and B, C and D showing an onion plant without the bar gene (left) and containing the bar gene (right) 0, 3 and 10 days respectively after spraying with 0.05% vv solution of the herbicide Buster.

Putative transgenic plants were produced from both experiments 3 from 994 and 4 from 9911. Southern Blot analysis of clones of one transformant from each experiment demonstrated that the gfp gene was present in plants from both experiments and that both cultivars could be transformed (FIG. 5). When this blot was subsequently reprobed for the presence of the bar gene (FIG. 6) only the plants selected solely on the basis of the herbicide resistance were shown to contain the bar gene. These plants were then used for herbicide leaf paint assays and subsequently sprayed with recommended field application rates of the herbicide Buster (active ingredient phosphinothricin). Control plants containing no bar gene showed noticeable wilt after 3 days and were essentially dead after 10 days following application of the herbicide, whilst the plants that contained the bar gene and had been selected on herbicide did not appear to be harmed and grew normally (FIG. 7).

EXAMPLE 6

Demonstration that Transformation is Independent of Cultivar, Construct, T-DNA and Selective Agent.

Discussion

We have developed a repeatable transformation system for onion. The regenerating primary transformants appear to be phenotypically normal. The GFP expression, as a visual, selectable marker, enabled post transformation selection conditions to be optimised. The GFP marker has also proved useful in the selection of transgenic plants from other species that are difficult to transform (Vain et al. 1998). Selection conditions have now been established, which enable the identification of transformants solely on their ability to root in selective media (example 5).

This method of producing transgenic onions is repeatable and efficient. It takes a short time to produce transgenic plants and utilizes techniques have been shown to be cultivar independent (Example 6).

For example, this described process of transformation can be used with any species within the *Allium* and is not limited to onions. Work has shown that the described process of transformation is genotype independent.

It is to be understood that the scope of the invention is not limited to the described embodiments and therefore that numerous variations and modifications may be made to these embodiments without departing from the scope of the invention as set out in this specification.

INDUSTRIAL APPLICABILITY

The invention provides a novel method of transforming plants of the genus *Allium* and in particular onion plants. Also provided are plants transformed by the method. This allows *Allium* crop species which are an economically important vegetable species to be transformed by a variety of genes for improvement of *Allium* crop varieties.

REFERENCES

Barandiaran X, Dipietro A, Martin J (1998). *Plant Cell Reports* 17, 737-741.
Dommisse E M, Leung D M, Shaw M L, Conner A J (1990). *Plant Science* 69, 249-257.
Eady C C, Lister C E (1998a). *Plant Cell Reports* 18: 117-121.
Eady C C, Lister C E (1998b). In: *Proceedings of the Second International Symposium on Edible Alliaceae*, Adelaide Australia. *Acta Horticulturae* In press
Eady C C, Suo Y, Butler R C (1998). *Plant Cell Reports* 18: 111-116.
Eady C C, Lister C E, Suo Y, Schaper D (1996). *Plant Cell Reports* 15, 958-962.
Grant J, Brown A, Grace J (1984). *Australian Journal of Botany* 32, 665-677.
Haseloff J, Siernering K R, Prasher D C, Hodge S (1997). *Proceedings of the National Academy of Sciences of the United States of America* 94, 2122-2127.
Hong W, Debergh P (1995). *Plant Cell Tissue & Organ Culture* 43, 21-28.
Klein T M, Wolf E D, Wu R, Sanford J C (1987). *Nature* 327, 70-73.
Murashige T, Skoog F (1962). *Physiol. Plant* 15, 473-497.
Saker M M (1998). *Biologia Plantarum* 40, 499-506.
Timmerman G M, Frew T J, Miller A L, Weeden N F, Jermyn W A (1993). *Theoretical and Applied Genetics* 85, 609-615.
Vain P, Worland B, Kohli A, Snape J W, Christou P (1998). *Theoretical & Applied Genetics* 96, 164-169.
Xue H M, Araki H, Kanazawa T, Harada T, Yakuwa T (1997). *Journal of the Japanese Society for Horticultural Science* 66, 353-358.

The invention claimed is:

1. A method of transforming an *Allium* plant comprising the following steps:
   (a) transforming embryo cells of the *Allium* plant with DNA sequences via a vector or direct gene transfer to produce transformed plant material, wherein transformation is achieved by:
      (i) wounding the embryo cells and transferring the embryo cells into a suspension of *Agrobacterium*,
      (ii) transferring the embryo cells from step (i) to a culture medium;
      (iii) co-cultivating the embryo cells and the *Agrobacterium* attached to the embryo cells for a period of 1-12 days from the end of step (ii);
   (b) selecting the transformed plant material derived from step (a), by transferring the embryo cells to a selection medium containing the appropriate selection agents to kill the agrobacteria and preferentially grow the transgenic embryo cells to produce transformed plant material;
   (c) culturing the transformed plant material from (b) to produce secondary embryos and regenerating transformed plant material from the secondary embryos; and
   (d) obtaining a transformed *Allium* plant from the secondary embryo;
   wherein the method of transforming is carried out without a passage through a callus phase.

2. A method of transforming an *Allium* plant comprising the following steps:
   (a) transforming embryo cells of the *Allium* plant with DNA sequences via a vector or direct gene transfer to produce transformed plant material, wherein transformation is achieved by:
      (i) wounding the embryo cells and transferring the embryo cells into a suspension of *Agrobacterium* containing a plasmid with a functional T-DNA region that is capable of transfer to plant cells,
      (ii) transferring the embryo cells from step (i) to a culture medium;
      (iii) co-cultivating the embryo cells and the *Agrobacterium* attached to the embryo cells for a period of 1-12 days from the end of step (ii);
   (b) selecting the transformed plant material derived from step (a), by transferring the embryo cells to a selection medium containing the appropriate selection agents to kill the agrobacteria and preferentially grow the transgenic embryo cells to produce transformed plant material;
   (c) culturing the transformed plant material from (b) to produce secondary embryos and regenerating transformed plant material from the secondary embryos; and
   (d) obtaining a transformed *Allium* plant from the secondary embryo;
   wherein the method of transforming is carried out without a passage through a callus phase.

3. A method of transforming an *Allium* plant comprising the following steps:
   (a) transforming embryo cells of the *Allium* plant with DNA sequences via a vector or direct gene transfer to produce transformed plant material, wherein transformation is achieved by:
      (i) wounding the embryo cells and transferring the embryo cells into a suspension of Agrobacterium,
      (ii) transferring the embryo cells from step (i) to a culture medium;
      (iii) co-cultivating the embryo cells and the *Agrobacterium* attached to the embryo cells for a period of 1-12 days from the end of step (ii);
   (b) identifying the transformed plant material derived from step (a), by detecting the expression of a reporter gene;
   (c) culturing the transformed plant material from (b) to produce secondary embryos and regenerating transformed plant material from the secondary embryos; and
   (d) obtaining a transformed *Allium* plant from the secondary embryo;
   wherein the method of transforming is carried out without a passage through a callus phase.

4. The method of any one of claims 1-3, wherein the DNA sequences comprise a selectable gene.

5. The method of claim 4, wherein the selectable gene is a herbicide resistance gene.

6. The method of claim 5, wherein the herbicide resistance gene is the bar gene, the ppt gene, or a glyphosate resistance gene.

7. The method of claim 4, wherein the selectable gene is an antibiotic resistance gene.

8. The method of claim 7, wherein the antibiotic resistance gene is the nptll gene.

9. The method of claim 3, wherein the DNA comprises a reporter gene.

10. The method of claim 9, wherein the reporter gene encodes GFP or GUS.

* * * * *

UNITED STATES PATENT AND TRADEMARK OFFICE
CERTIFICATE OF CORRECTION

Page 1 of 1

PATENT NO.         : 7,737,328 B2
APPLICATION NO.    : 11/494734
DATED              : June 15, 2010
INVENTOR(S)        : Carolyn Elizabeth Lister and Colin Charles Eady It is certified that error appears in the above-identified patent and that said Letters Patent is hereby corrected as shown below:

Title page, item [73] Assignee - Change

New Zealand Institute for Crop and Food Research Limited to item [73] Assignee:

The New Zealand Institute for Plant and Food Research Limited

Signed and Sealed this
Fourth Day of September, 2012

David J. Kappos
*Director of the United States Patent and Trademark Office*